(12) United States Patent
Vreysen et al.

(10) Patent No.: US 7,723,518 B2
(45) Date of Patent: May 25, 2010

(54) PREPARATION OF 9-HYDROXY-3-(2-HYDROXYETHYL)-2-METHYL-4H-PYRIDO[1,2-A]PYRIMIDIN-4-ONE

(75) Inventors: Eduard Jozef Contantia Vreysen, Mol (BE); Joannes Petrus Van Dun, Lille (BE); Wim Albert Alex Aelterman, Lille (BE)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 11/574,936

(22) PCT Filed: Sep. 7, 2005

(86) PCT No.: PCT/EP2005/054423

§ 371 (c)(1),
(2), (4) Date: Mar. 8, 2007

(87) PCT Pub. No.: WO2006/027370

PCT Pub. Date: Mar. 16, 2006

(65) Prior Publication Data

US 2007/0260061 A1 Nov. 8, 2007

(30) Foreign Application Priority Data

Sep. 9, 2004 (EP) .................. 04104362

(51) Int. Cl.
*C07D 471/04* (2006.01)
(52) U.S. Cl. ...................................... 544/282
(58) Field of Classification Search ................. 544/282
See application file for complete search history.

(56) References Cited

FOREIGN PATENT DOCUMENTS

| EP | 0368388 | A3 | 10/1989 |
| WO | WO 95/14691 | * | 6/1995 |
| WO | WO 96/23784 | * | 8/1996 |

* cited by examiner

*Primary Examiner*—Mark L Berch
*Assistant Examiner*—Cecilia M Jaisle

(57) ABSTRACT

The present invention concerns a process for preparing crystalline 3-(2-chloro-ethyl)-9-hydroxy-2-methyl-4H-pyrido[1,2-a]pyrimidin-4-one substantially free of 2-acetylbutyrolactone.

6 Claims, No Drawings

PREPARATION OF 9-HYDROXY-3-(2-HYDROXYETHYL)-2-METHYL-4H-PYRIDO[1,2-A]PYRIMIDIN-4-ONE

CROSS REFERENCE TO RELATED APPLICATIONS

This application is the national stage of Application No. PCT.EP2005/054423, filed 7 Sep. 2005, which application claims priority from EP 04104362.1 filed 9 Sep. 2004.

BACKGROUND OF THE INVENTION

The present invention concerns a process for preparing crystalline 9-hydroxy-3-(2-hydroxyethyl)-2-methyl-4H-pyrido[1,2-a]pyrimidin-4-one substantially free of 2-acetylbutyrolactone. This product is a new intermediate for the preparation of 9-hydroxyrisperidone or paliperidone and that of 9-hydroxyrisperidone palmitate ester or paliperidone palmitate ester.

The previously described synthesis of the latter compounds involved the preparation of 3-(2-chloroethyl)-9-hydroxy-2-methyl-6,7,8,9-tetrahydro-4H-pyrido[1,2-a]pyrimidin-4-one. In EP-0,368,388 (U.S. Pat. No. 5,158,952) this starting material was prepared in situ by reacting 3-phenylmethoxy-pyridin-2-amine with 1.7 equivalents 2-acetyl-butyrolactone (3-acetyl-4,5-dihydro-2(3H)-furanone) in toluene in the presence of phosphoryl chloride, adding another 1.7 equivalents of 2-acetylbutyrolactone after five hours of stirring at 90° C., followed by hydrogenolysis of the benzyl group and concomitant reduction of the pyridine ring to a tetrahydropyridine ring. The resulting 3-(2-chloroethyl)-9-hydroxy-2-methyl-6,7,8,9-tetrahydro-4H-pyrido[1,2-a]pyrimidin-4-one was isolated as an oil which allowed further conversion to paliperidone and paliperidone palmitate ester in the laboratory.

During chemical development this process was altered. 2-Amino-3-hydroxypyridine was reacted with 2-acetyl-butyrolactone in the presence of p-toluenesulfonic acid in xylene to yield 9-hydroxy-3-(2-hydroxyethyl)-2-methyl-4H-pyrido[1,2-a]pyrimidin-4-one; this product proved to be poorly soluble in xylene resulting in deposit formation on the wall of the reaction vessel and discoloration of the reaction mixture to black.

The intermediate product was subsequently converted into the 2-chloroethyl derivative by reaction with thionyl chloride in dimethylformamide. This reaction was characterized by very severe smell hindrance, probably caused by reaction of residual 2-acetylbutyrolactone remaining from the previous step and nonreproducible yield and quality.

In order to solve the problems described in the previous paragraph, various solvent systems and acids were tested in which to conduct the reaction of 2-amino-3-hydroxypyridine with 2-acetyl-butyrolactone.

The tested solvent systems were:
a) toluene
b) 2-acetylbutyrolactone as solvent and reagent (no co-solvent)
c) propylene glycol monomethyl ether (PGMME)
d) 4-methyl-2-pentanol
e) xylene combined with 4-methyl-2-pentanol
f) dimethylacetamide
g) chlorobenzene
h) acetic acid
i) glyme
j) diglyme The tested acids were p-toluenesulfonic acid and acetic acid.

The results of the tests can be summarized as follows:
1) Solvent systems:
   a) Toluene suffered from the same problems as xylene, namely that the reaction product was very poorly soluble therein and was deposited on the walls of the reaction vessel.
   b) Conversion in the absence of a co-solvent varied between 53 and 77%. The process was characterized by excessive foaming.
   c) Conversion in PGMME varied from 36 to 67%.
   d) Conversion in 4-methyl-2-pentanol varied between 59 and 66%.
   e) Conversion in a mixture of xylene and 4-methyl-2-pentanol was about 62%.
   f) In dimethylacetamide, the conversion was only 38%.
   g) Conversion in chlorobenzene ranged from 55 to 81%, conversion being higher when equimolar amounts of both reagents were used and being lower when excess 2-acetylbutyrolactone was used. Interestingly, the reaction mixture remained homogeneous when chlorobenzene was the solvent.
   h) In acetic acid the conversion was only 22%.
   i) No conversion in glyme.
   j) Diglyme suffered from the same problems as xylene, namely that the reaction product was very poorly soluble therein and was deposited on the walls of the reaction vessel.
2) Acid systems: the conversion was 10% lower for the acetic acid system compared with the p-toluenesulfonic acid system.

Further optimisation of the reaction conditions taught us that optimal results could be obtained by reacting 1 mol equivalent of 2-amino-3-hydroxypyridine with a slight excess (e.g. 1.05 mol equivalent) of 2-acetylbutyrolactone in about 1.75 L/mol equivalent of chlorobenzene in the presence of about 0.03 mol equivalent p-toluene-sulfonic acid monohydrate during 19 hours at 125-135° C. with removal of water using a reverse water separator.

Three different work-up procedures were evaluated next:
k) Cooling the reaction mixture to about 80° C., adding 0.25 L/mol equivalent 2-propanol, reheating to reflux, allowing spontaneous cooling, collecting the resulting crystals,
l) Cooling the reaction mixture and collecting the resulting crystals, and
m) Cooling the reaction mixture to about 80° C., adding 0.25 L/mol equivalent PGMME, reheating to reflux, allowing spontaneous cooling, collecting the resulting crystals.

In procedure l), the product proved to contain more residual 2-acetylbutyrolactone and 2-amino-3-hydroxypyridine than product obtained in procedures k) and m).

Finally, process k) was further optimised by adding a mixture of activated carbon and filter agent (dicalite speed plus).

SUMMARY OF THE INVENTIONS

Thus, the present invention provides a process for preparing crystalline 9-hydroxy-3-(2-hydroxyethyl)-2-methyl-4H-pyrido[1,2-a]pyrimidin-4-one substantially free of 2-acetylbutyrolactone comprising the steps of
a) reacting 2-amino-3-hydroxypyridine with a slight excess of 2-acetylbutyrolactone

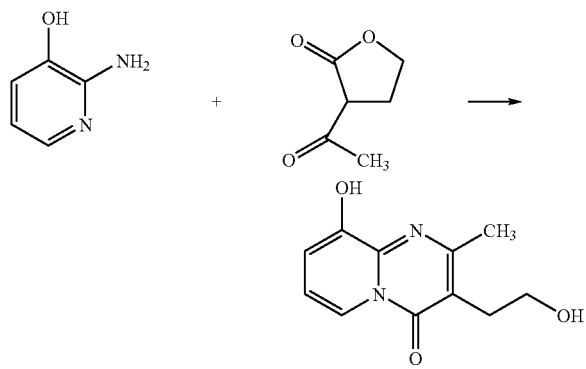

in an organic solvent allowing azeotropic removal of water in the presence of a catalytic amount of an acid at reflux temperature while azeotropically removing the water formed during the reaction;
b) working up the reaction mixture;
c) allowing 9-hydroxy-3-(2-hydroxyethyl)-2-methyl-4H-pyrido [1,2-a]pyrimidin-4-one to crystallize while cooling;
d) collecting and washing the crystals with the organic solvent and drying in vacuo, yielding 9-hydroxy-3-(2-hydroxyethyl)-2-methyl-4H-pyrido [1,2-a]pyrimidin-4-one; containing less than 0.3% residual 2-acetylbutyrolactone.

Preferably, the organic solvent is chlorobenzene and the acid is p-toluenesulfonic acid.

Further, the working up step comprises adding an alcohol and heating to reflux. In particular, the working up step comprises
b-1) adding an alcohol and activated carbon and a filter agent, and heating to reflux;
b-2) filtering at a temperature of 90 to 95° C. and washing the filter cake with said organic solvent.

Preferably, the alcohol added is 2-propanol or propylene glycol monomethyl ether.

The present invention also provides crystalline 9-hydroxy-3-(2-hydroxyethyl)-2-methyl-4H-pyrido[1,2-a]pyrimidin-4-one substantially free of 2-acetylbutyrolactone, in particular crystalline 9-hydroxy-3-(2-hydroxyethyl)-2-methyl-4H-pyrido[1,2-a]-pyrimidin-4-one having a purity >97% and containing less than 0.3% residual 2-acetylbutyrolactone.

EXPERIMENTAL PART

EXAMPLE 1

In a reaction vessel equipped with a dropping funnel and a reverse water-separator, 2-amino-3-hydroxypyridine (110.12 g; 1 mol) was added to chlorobenzene (1500 ml) at room temperature. 2-Acetylbutyrolactone (134.53 g; 1.05 mol) was added dropwise to this mixture from the dropping funnel while stirring. The dropping funnel was rinsed with chlorobenzene (250 ml) and the resulting solution was added dropwise to the previously obtained mixture. Next, p-toluenesulfonic acid monohydrate (5.7 g; 0.03 mol) was added, and the resulting mixture was heated to reflux temperature (refluxing starting at 125° C.). The reaction mixture was refluxed for 19 hours, while the water liberated during the course of the reaction was collected in the reverse water-separator. The mixture was allowed to cool to about 80° C. and then there were added 2-propanol (250 ml), activated carbon (Norit A™ supra, 25 g) and filter agent (dicalite speed plus; 2.5 g). The mixture was heated to reflux (100° C.) during 30 minutes. The reaction mixture was filtered at a temperature of 90 to 95° C. and the filter cake was washed with chlorobenzene (100 ml; 80° C.). The combined filtrate was allowed to cool to room temperature. Crystallization of the reaction product started at about 40-45° C. and was left to continue for 18 hours at room temperature. The crystals were collected and washed with chlorobenzene (100 ml) and dried in vacuo at 50-60° C. for 24 hours, yielding 164.2 g (73.6%) 9-hydroxy-3-(2-hydroxyethyl)-2-methyl-4H-pyrido[1,2-a]pyrimidin-4-one; mp 150° C.; purity >97% (LC % w/w); residual 2-amino-3-hydropyridine: 0.85%; sum of other impurities <0.52%; residual 2-acetylbutyrolactone was 0% (GC % w/w).

EXAMPLE 2

The procedure of Example 1 was transferred to the chemical production plant where it was repeated at full scale (35 batches) using appropriate equipment. The average yield of 9-hydroxy-3-(2-hydroxyethyl)-2-methyl-4H-pyrido [1,2-a] pyrimidin-4-one was 67.0%; the purity of the desired reaction product exceeded 97% and residual 2-acetylbutyrolactone amounted to 0.14% (average of 35 batches).

We claim:
1. A process for preparing crystalline 9-hydroxy-3-(2-hydroxyethyl)-2-methyl-4H-pyrido[1,2-a]pyrimidin-4-one substantially free of 2-acetylbutyrolactone comprising the steps of
a) reacting 2-amino-3-hydroxypyridine with a slight molar excess of 2-acetylbutyrolactone while azeotropically removing the water formed during the reaction

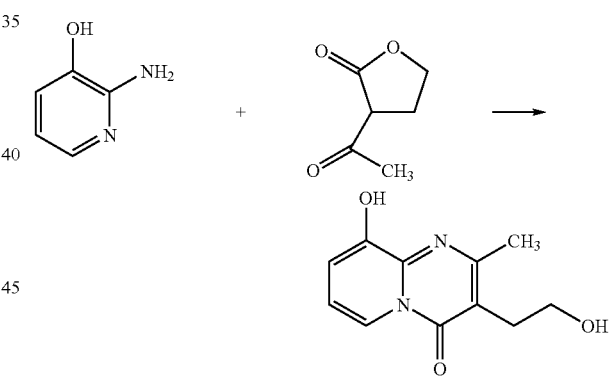

in an organic solvent selected from the group consisting of 4-methyl-2-pentanol; a mixture of xylene and 4-methyl-2-pentanol; and chlorobenzene; in the presence of a catalytic amount of an acid at reflux temperature to form 9-hydroxy-3-(2-hydroxyethyl)-2-methyl-4H-pyrido[1,2-a]-pyrimidin-4-one;
b) working up the reaction mixture wherein the working up step comprises adding an alcohol and heating to reflux;
c) allowing 9-hydroxy-3-(2-hydroxyethyl)-2-methyl-4H-pyrido[1,2-a]-pyrimidin-4-one to crystallize while cooling;
d) collecting and washing the crystals with the organic solvent and drying in vacuo, yielding 9-hydroxy-3-(2-hydroxyethyl)-2-methyl-4H-pyrido[1,2-a]-pyrimidin-4-one; containing less than 0.3% residual 2-acetylbutyrolactone by weight.
2. The process according to claim 1 wherein the organic solvent is chlorobenzene.

3. The process according to claim 1 wherein the acid is p-toluenesulfonic acid.

4. The process according to claim 1 wherein the working up step comprises
- b-1) adding an alcohol and activated carbon and a filter agent, and heating to reflux;
- b-2) filtering at a temperature of 90 to 95° C. to obtain a filter cake and washing the filter cake with said organic solvent.

5. The process of claim 1 wherein the alcohol added is 2-propanol or propylene glycol monomethyl ether.

6. Crystalline 9-hydroxy-3-(2-hydroxyethyl)-2-methyl-4H-pyrido[1,2-a]-pyrimidin-4-one having a purity >97% by weight and containing less than 0.3% residual 2-acetylbutyrolactone by weight.

* * * * *